United States Patent
Chadeayne

(10) Patent No.: US 9,301,909 B2
(45) Date of Patent: Apr. 5, 2016

(54) COMPOSITIONS AND METHODS FOR MITIGATING ADVERSE EFFECTS OF EXPOSURE TO OXIDIZERS, SUCH AS CHLORINATING AND/OR BROMINATING AGENTS

(71) Applicant: Andrew R. Chadeayne, Arlington, VA (US)

(72) Inventor: Andrew R. Chadeayne, Arlington, VA (US)

(*) Notice: Subject to any disclaimer, the term of this patent is extended or adjusted under 35 U.S.C. 154(b) by 0 days.

(21) Appl. No.: 13/707,716

(22) Filed: Dec. 7, 2012

(65) Prior Publication Data

US 2013/0095055 A1 Apr. 18, 2013

Related U.S. Application Data

(63) Continuation-in-part of application No. PCT/US2011/046042, filed on Jul. 29, 2011.

(60) Provisional application No. 61/369,360, filed on Jul. 30, 2010.

(51) Int. Cl.
| | |
|---|---|
| A61K 8/49 | (2006.01) |
| A61Q 15/00 | (2006.01) |
| C11D 3/20 | (2006.01) |
| C11D 7/26 | (2006.01) |
| C11D 11/00 | (2006.01) |

(52) U.S. Cl.
CPC .............. *A61K 8/4973* (2013.01); *A61Q 15/00* (2013.01); *C11D 3/2086* (2013.01); *C11D 7/265* (2013.01); *C11D 11/0017* (2013.01)

(58) Field of Classification Search
None
See application file for complete search history.

(56) References Cited

U.S. PATENT DOCUMENTS

| | | | |
|---|---|---|---|
| 4,295,985 A | 10/1981 | Petrow et al. | |
| 4,367,157 A | 1/1983 | Sherman | |
| 4,547,364 A | 10/1985 | Brown | |
| 4,690,818 A | 9/1987 | Puchalski, Jr. et al. | |
| 5,804,172 A | 9/1998 | Ault | |
| 6,110,966 A * | 8/2000 | Pollock | 514/474 |
| 7,101,822 B2 | 9/2006 | Devisme et al. | |
| 2004/0034094 A1 | 2/2004 | Gupta | |
| 2009/0197946 A1 | 8/2009 | Bartolomeo | |

FOREIGN PATENT DOCUMENTS

| | | | |
|---|---|---|---|
| JP | 08198738 A * | 8/1996 | |
| JP | 08198743 A | 8/1996 | |
| JP | 2001079568 A | 3/2001 | |
| JP | 2004-024786 A | 1/2004 | |
| JP | 2010-126506 A | 6/2010 | |
| WO | 02055041 A2 | 7/2002 | |

OTHER PUBLICATIONS

Abstract translation of JP08198738 Jun. 8, 1996.*
Machine translation of JP08198738 Jun. 8, 1996.*
Wood M, "Cleaner chicken ahead," Agricultural Research; vol. 42(9), Sep. 1994, p. 20-21 (2 sheets).
Kenworthy T, "Chlorine Detoxification," available at www.kenworthywellness.com/chlorine-detox.html, retrieved on Apr. 22, 2013 (3 sheets).
Abstract of JP 2001 079568 A.
Land et al., "Using Vitamin C to Neutralize Chlorine in Water Systems", Retrieved from the Internet: http://www.fs.fed.us/t-d/pubs/html/05231301/05231301.html, Feb. 27, 2015.
English Abstract of JP 08-198743A.
English Abstract of JP 2004024786A.
English Abstract of JP 2010126506A.

* cited by examiner

*Primary Examiner* — Mina Haghighatian
*Assistant Examiner* — Luke Karpinski
(74) *Attorney, Agent, or Firm* — J.A. Lindeman & Co., PLLC

(57) ABSTRACT

Disclosed are methods of mitigating the effects of exposure to oxidizing agents, chlorinating and/or brominating agents on biological and/or synthetic fibers, by treating the body and/or clothing fibers with an effective amount of a composition comprising compounds of formula A. Also disclosed are compositions comprising compounds of formula A, for use in treating biological and/or synthetic fibers to mitigate the effects of exposure to chlorinating and/or brominating agents.

6 Claims, No Drawings

COMPOSITIONS AND METHODS FOR MITIGATING ADVERSE EFFECTS OF EXPOSURE TO OXIDIZERS, SUCH AS CHLORINATING AND/OR BROMINATING AGENTS

CROSS-REFERENCE TO RELATED APPLICATION

This application is a continuation-in-part of International Application No. PCT/US11/46042, filed Jul. 29, 2011, which claims priority to U.S. Provisional Application 61/369,360, filed Jul. 30, 2010.

TECHNICAL FIELD

The disclosure relates to compositions and methods for decreasing or eliminating adverse effects of oxidizers, such as chlorinating and/or brominating agents, on biological and synthetic fibers.

BACKGROUND

Biological and synthetic fibers may be exposed to chlorinating and/or brominating agents in a variety of ways.

For example, swimming is a popular form of exercise and pastime. By its nature, swimming requires immersing oneself in a body of water. People may swim in either natural bodies of water (such as lakes, oceans, rivers, etc.), or man-made swimming pools.

Man-made swimming pools (including traditional swimming pools, hot tubs, etc., collectively referred to generally herein as "pools") are usually smaller than naturally occurring bodies of water. They are also usually self-contained structures, consisting of a finite body of water separated from the surrounding environment, for example by walls. Pools provide an aqueous environment that is kept within a biologically habitable temperature range, such as about 65-90° F. Some pools may be kept cooler or warmer. For example, a hot tub may be maintained at more than 90° F.

A swimmer brings a variety of living and non-living substances into the pool. For example, the swimmer's skin, hair, saliva, urine, sweat, and other secretions may come into contact with the pool water. Owing to the aqueous medium and adequate temperature, pools provide a suitable environment for living organisms, such as bacteria, to thrive.

Pools are usually treated with chemicals chosen to prevent the growth of harmful organisms, such as bacteria. Properly used, these chemicals keep the pool water substantially free from harmful contaminants. For example, many pools are treated with chlorinating agents (e.g., chlorine, hypochlorite salts such as calcium hypochlorite or sodium hypochlorite, hypochlorous acid) or brominating agents (e.g., bromine, salts comprising bromine, etc).

The chemicals used to treat pool water work by reacting with certain molecules that come into contact with the pool water. For example, these chemicals may react with bacteria's biologically important molecules, thereby killing the bacteria.

In addition to reacting with bacteria and other contaminants, however, some pool chemicals react with elements of the swimmer, such as the swimmer's body and/or the swimmer's attire. For example, the fibers that make up the exterior of the body, such as skin, hair, eyes, and nails (collectively referred to herein as "body fibers," and intending to include keratinous fibers that make up the hair, skin, and nails, as well as mucous membranes), comprise proteins. By way of example, human hair is made largely from alpha keratin (α-keratin). Those proteins are made from amino acids. All amino acids, including those making up proteins, have one or more N—H bonds. In α-keratin, the most abundant amino acid is cystine, which accounts for about 15% of the protein. Monomeric L-cystine has two N—H bonds. The oxidized dimmer of cystine has four N—H bonds. When present within a protein, each cystine residue has one N—H bond.

The N—H bonds in the amino acids in body fibers can react with the chemicals found in pool water. For example, one or more N—H bonds in an amino acid in the protein of hair or skin can react with a chlorinating agent used in pool water to form N—Cl, an amino chloride. Notably, the reacted amino acid, now containing an N—Cl bond, is still part of the protein in the hair or skin.

Although a swimmer can rinse the residual pool water from his or her skin, hair, attire, etc., after swimming, such rinsing may not effectively eliminate all the adverse effects of exposure to the chemically-treated pool water. For example, where the body's proteins have chemically reacted with the pool chemicals, they are physically changed but, at least in part, remain part of the body, i.e. they are not all rinsed away such as during normal showering.

Those remaining pool chemicals can be released throughout the day, for example as a result of exposing the skin, hair, etc., to moisture, e.g. water. As discussed above, after swimming in a pool with a chlorinating and/or brominating agent, proteins of the human body may become chlorinated and/or brominated. Subsequent exposure of those chlorinated and/or brominated amino groups to water (e.g. rain or sweat) may release these volatile chemicals, which may be corrosive or irritating.

Some of these corrosive molecules may be harmful to body and/or textile fibers (e.g. clothing such as swimming attire), or may cause an unpleasant sensation upon contact with the body and/or clothing fibers. Additionally, some of the volatile molecules may be perceived by the nose when liberated from the body and/or clothing, giving rise to odors. These odors are commonly referred to as simply "chlorine" or "pool odor," and are considered a more chemical odor, rather than the type of odor naturally produced by the body.

Also, when pool chemicals, such as chlorine or bromine, react with the biological molecules forming the skin and/or eyes, those reactions may cause irritation. For example, some swimmers report itchy or inflamed skin following swimming in pools. Some swimmers indicate that mucous membranes, such as the sensitive nasal skin, become itchy and irritated following swimming.

Although some people have reported liking "pool odor," as reminiscent of the pleasures associated with swimming itself, others do not like pool odor or, if strong enough, find the odor irritating, such as to the eyes and lungs. Additionally, since the chemicals liberated may irritate the skin and/or damage the hair, many people wish to prevent "pool odor" and/or the symptoms associated with it.

As discussed above, rinsing or washing, e.g. body fibers, does not by itself completely eliminate pool odor and/or skin irritation. Mitigating (i.e. decreasing to some extent or eliminating entirely) the effects of exposure to chlorinating and/or brominating agents requires reversing the chemical reaction between those chemicals and the proteins making up the human body. This requires converting the amino-halide bonds, e.g., chloramine (N—Cl) and/or bromamine (N—Br) groups into amino (N—H) groups. However, the soaps, shampoos, and conditioners currently known do not effectively convert N—Cl and/or N—Br bonds on body fibers back into N—H bonds. Accordingly, N—Cl and/or N—Br remain bonded to the body fibers following rinsing, washing, shampooing, and/or conditioning the body fibers, such as the skin and/or hair.

Some known shampoo and soap formulations are directed to mitigating the effects of exposure to chlorinating and/or brominating agents. For example, U.S. Pat. No. 4,295,985 discloses "a method of removal of chlorine retained by human skin and hair after exposure to chlorinated water, and soap and shampoo compositions adapted to effect said removal." That patent teaches applying urea and thiosulfate salts to the hair and/or body following exposure to chlorinating agents.

Other known formulations have sought to remove minerals from hair in an effort to prevent discoloration of the hair. For example, U.S. Pat. No. 5,804,172 discloses compositions aimed at removing mineral deposits from hair exposed to hard water, particularly the calcium, magnesium, iron, and copper present in some municipal water sources. That patent discloses compositions including four ingredients, which are said to remove minerals from the hair due to the "synergistic combination" of ingredients. Within those compositions, a reducing agent, such as ascorbic acid, is included in an amount chosen to reduce oxidized cysteine-iron bonds. The patent discloses four-component compositions comprising 2.1 percent w/w of ascorbic acid, which is said to be sufficient to reduce the oxidation state of iron ions bonded to hair.

Additional known formulations have sought to remove chlorine from hair by treating the hair with ammonium lauryl sulfate, cocamide diethanolamine, sodium bicarbonate, cocobetaine, and water. See U.S. Pat. No. 4,547,364.

Finally, a host of other formulations promise to treat damaged hair and/or skin following exposure to swimming pools by using various combinations of ingredients. For example, U.S. Pat. No. 4,690,818 discloses a combination of hair and skin conditioners and moisturizers, namely, "a combination of cocodimonium hydrolyzed keratin and a mixture of monosaccharides and disaccharides . . . ."

Further, chlorine (including, for example, gaseous or solvated $Cl_2$, chlorine-comprising oxidizing agents, and salts thereof) has a multitude of uses in both household and industrial applications. For example, it can be used for disinfecting, whitening, bleaching, and clarifying materials. Chlorine is often used as an antimicrobial agent. For example sodium hypochlorite (a chlorinating agent) is known to kill a broad array of microbes. Owing to the efficacy, cost, and versatility of chlorinating agents, they are amazingly attractive reagents for a variety of home and industrial applications.

A down side to using chlorinating agents in the home and industry is that they can react with many of the materials to which they are exposed—often materials that the user would like to keep free from chlorination. Because materials and surfaces that are exposed to chlorine and chlorinating agents undergo a chemical reaction with the chlorine, their chemical composition becomes altered. Part of the chlorine and/or chlorinating agent becomes bound to the material or surface. Accordingly, one cannot simply wash away the residual chlorine. The bound chlorine must first be liberated before it can be washed away.

By way of non-limiting example, one may desire to kill microbes present on a particular surface, without altering the makeup of the surface that is disinfected. A user may, for example, wish to sterilize biological materials, metal, glass, textiles, floors, etc. with a chlorinating agent, but not wish to chlorinate the surface. If the chlorine is not liberated, it can react with other molecules that later come into contact with the material or surface.

And yet further, in the food industry, it may be desired to chlorinate the water that is used to chill poultry carcasses, such as chicken, but chicken producers would like to avoid chlorinating the biological tissues making up the chicken. Poultry is an important part of the worldwide animal food market. The poultry industry raises chickens, kills them, and then processes them into a form that is both convenient and safe for the consumer to use in preparing meals. Converting live chickens into healthy food presents challenges to the chicken industry. In particular, poultry provides an excellent medium for the growth of microorganisms, such as *Pseudomonas, Staphylococcus, Micrococcus, Acinetobacter, Moraxella*, and *Salmonella*.

Even a healthy chicken harbors a considerable amount and variety of microorganisms, such as bacteria. These bacteria can be present on the chicken's feathers, feet, skin, and/or innards. During the slaughtering and processing procedures, bacteria present on the chicken may be carried along to subsequent processing steps. Preventing microbial contamination is immensely important throughout each aspect of chicken processing.

When the birds have reached "harvest" time, they are deprived of food and water. This allows their digestive tracts to empty so that less feces and undigested food enter the later processing steps. Minimizing these products of the digestive system reduces the overall potential for contaminating the chicken during processing. The chickens are usually stunned before killing them. Stunning knocks the birds unconscious but it does not kill them. The birds are killed either by hand or by a mechanical rotary knife that cuts the jugular veins and the carotid arteries at the neck. The birds are permitted to bleed for a fixed amount of time, depending on size and species (e.g., bleeding times of about 1.5 minutes for broilers).

Following bleeding, the birds go through scalding tanks. These tanks contain hot water that softens the skin, making it easier to remove the feathers. During scalding, the temperature of the water is carefully controlled, at least in part to control the chickens' color. If retaining the yellow skin color is desired, a soft-scald is used (about 50° C. or 122° F.). If a white bird is desired, a higher scald temperature is used, resulting in the removal of the yellow pellicle. Turkeys and spent hens (egg-laying birds that have finished their laying cycles) are generally run at higher temperatures-59° to 60° C. (138° to 140° F.).

After bleeding and scalding, the carcasses go through the feather-picking machines, which beat off the feathers with rubber fingers. Throughout the feathering process, the carcasses are moved through a sequence of machines, each optimized for removing different sets of feathers. Then, the carcasses may be singed by passing through a flame that burns off any remaining feathers.

After feathering, the chickens' heads are pulled off mechanically; their legs are removed with a rotary knife (much like a meat slicer). Then, the preen, or oil, gland is removed from the tail; the vent is opened so that the internal organs can be removed ("evisceration").

Evisceration can be performed either by hand or by using an automated mechanical device. Automated evisceration lines can operate at a rate of about 70 birds per minute. The evisceration equipment is cleaned (with relatively high levels of chlorine) after each bird.

After eviscerating the chicken, the remaining carcasses are further cleaned. The viscera are separated from the carcasses. The edible offal are removed from the inedible offal. (The heart, stomach, and liver are all considered edible offal and are independently processed). Stomachs are usually cut open and the inside yellow lining of the stomach along with the stomach contents are removed.

The lungs and kidneys are removed separately from the other visceral organs using a vacuum pipe. The carcasses are then washed thoroughly. After the carcasses have been washed, they are chilled to a temperature below 4° C. (40° F.). The two main methods for chilling poultry are water chilling and air chilling. Water chilling is performed in chlorinated water.

Water chilling is used throughout North America and involves a pre-chilling step in which a countercurrent flow of cold water is used to lower the temperature of the carcasses. The carcasses are then moved into a chiller—a large tank specifically designed to move the carcasses through in a specific amount of time. Multiple tanks are often used to minimize cross-contamination.

A specified overflow of water for each tank is required by law in the United States and Canada. Although this renders the chilling process very water-intensive, it helps to minimize bacterial cross-contamination by diluting the microorganisms washed off the carcasses, thereby preventing recontamination.

During chilling, raw carcasses—already de-feathered and eviscerated, as described above—are submerged in cold water. The bath chills the birds to 40° F. or lower, preserving its freshness and lengthening its shelf life. The carcasses entering this chilling bath may be warm because the bird's living temperature was warm and, after killing, hot water was used in scalding/defeathering. Owing to the warm temperature of these carcasses, they provide a suitable temperature for bacterial proliferation.

In poultry processing plants, thousands of poultry carcasses share communal chiller tubs. To prevent microorganisms carried by some chickens from contaminating the water and infecting other birds in the bath, many processors use chlorine to sanitize the water. This bath "is a critical point in the plant's control of cross-contamination by these microorganisms." Wood, M., *Agricultural Research*, September, 1994. In some commercial plants, the tanks are about 4 ft.×10 ft.×40 ft. and contain approximately 100,000 gallons of chilled, chlorinated water at around 33° F. They can have as many as a few thousand chickens in them at one time, on a continuous basis, for three shifts a day, with one two-hour cleanup period every 24 hours. The U.S.D.A. requires the plant operators to maintain a 38 ppm total chlorine residual in these tanks to provide adequate sanitation. Accordingly, during the chilling phase, the chicken is soaked in chlorinated water.

Exposing the chicken carcass to chlorinated water can lead to undesirable effects on the chicken ultimately entering the marketplace. In addition to reacting with bacteria and other contaminants, as desired, any chlorine present in the chiller water reacts with the body fibers of the eviscerated chicken. The body fibers that make up the exterior of the chicken comprise proteins made from amino acids, which, as described above, have one or more N—H bonds.

Similarly to that described above with regard to swimming, the N—H bonds in the amino acids making up chicken protein can react with the chlorine in chlorinated water. For example, one or more N—H bonds in an amino acid in the protein of the chicken can react with a chlorinating agent to form N—Cl, an amino chloride. Notably, the reacted amino acid, now containing an N—Cl bond, is still part of the chicken protein.

As also described above, although the residual chlorinated water can be rinsed off after a chicken is removed from the chiller, that sort of rinsing may not effectively eliminate all the adverse effects of exposure of the chicken carcass to the chemically-treated water. For example, where the chicken's proteins have chemically reacted with one or more chlorinating agents, they are physically changed but, at least in part, remain part of the chicken, i.e. they are not all rinsed away by normal rinsing.

The remaining chicken-bound chemicals can be released after the chicken is packaged and sent to the marketplace. For example, chlorine-containing molecules may be released by exposing the chicken to additional water, pH changes, or merely allowing for the passage of time. As discussed above, after exposing chicken to chlorinated water, the chicken's protein may become chlorinated. Subsequent exposure of those chlorinated amino groups to air and water may release chlorine containing chemicals, which may cause packaged chicken to have undesirable properties. For example, the chicken may have an undesirable odor (e.g., of "chlorine" or "bleach"), the chicken may lose depth of color, and/or the chicken may include residual chloride and/or hypochlorite. Some of these released molecules may be harmful to the chicken meat.

Faced with the undesirable post-processing chlorine smell and taste, some members of the chicken industry have attempted to process chickens without using chlorinating agents. But, using chlorinated water during at least the chilling process has proven so effective as an antimicrobial, that for safety reasons it is desired to continue to use this process. Accordingly, there remains a need to eliminate the residual undesirable affects of chlorine on the chicken.

However, there still exists a need for a convenient and effective method for mitigating the effects of chlorinating and/or brominating agents and other adverse effects on biological fibers (e.g., skin and eye itching and irritation) and/or synthetic fibers, such as textiles exposed to chlorinating and/or brominating agents, or water having chlorinating and/or brominating agents in it.

There remains a need in various industries, therefore, to mitigate adverse effects of exposure to oxidizers, such as chlorinating and brominating agents.

DESCRIPTION

Effective treatments for mitigating adverse effects of exposure of biological and/or synthetic fibers to oxidizers, such as chlorinating and/or brominating agents, have now been discovered. Specifically, it has been discovered that these effects may be mitigated by converting the amino chloride (N—Cl) and/or amino bromide groups (N—Br) bonded to such fibers back into amino (N—H) groups. Although not intending to be bound by theory, it is believed that this conversion reverses the effects of chlorinating and/or brominating agents because eliminating the N—Cl and/or N—Br groups from such fibers prevents those groups from reacting with water to liberate corrosive, odorous, or irritating chemicals throughout daily intercourse. Thus, the compositions and methods described herein are useful for reducing, dechlorinating, and deodorizing biological and synthetic fibers. When combined with a preceding oxidizing (e.g., bleaching) step, the compositions and methods are also useful for sanitizing the surface of materials comprising biological and synthetic fibers According to one aspect of the disclosure, treatment compositions for mitigating adverse effects of exposure to chlorinating and/or brominating agents are disclosed. Said treatment compositions may be applied to biological and/or synthetic fibers. Treatment compositions according to various embodiments of the disclosure comprise an effective amount of ascorbic acid. As used herein, unless otherwise specified, where the term "ascorbic acid" is used, Applicant also contemplates salts, such as sodium ascorbate, degradation products, and derivatives of ascorbic acid, such as those represented by the following formula A:

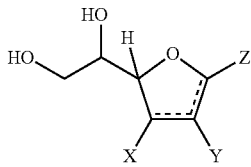
(A)

In the above formula A, each of groups X, Y, and Z is independently chosen from carbonyl or OR; and each dashed line may either be a bond (resulting in an overall double bond) or not a bond (resulting in an overall single bond), and R is chosen from a metal (e.g., lithium, sodium, potassium, magnesium, calcium) or a hydrogen atom (resulting in an alcohol).

For example, where the disclosure illustrates a method or composition comprising ascorbic acid, compositions and methods having one or more of the following illustrative compounds are also contemplated:

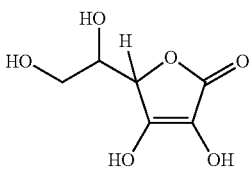
A-1

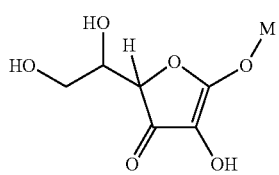
A-2

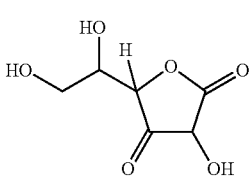
A-3

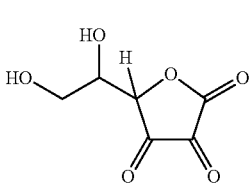
A-4

Notably, the above formula A and examples A-1, A-2, A-3, and A-4 do not show the stereochemistry at each of the stereogenic centers, because each and every combination of stereoisomers, including but not limited to (5R)-[(1S)-1,2-dihydroxyethyl]-3,4-dihydroxyfuran-2(5H)-one, Sodium (2R)-2-[(1S)-1,2-dihydroxyethyl]-4-hydroxy-5-oxo-2H-furan-3-olate, or Calcium (2R)-2-[(1S)-1,2-dihydroxyethyl]-4-hydroxy-5-oxo-2H-furan-3-olate, are intended to be within the scope of the disclosure.

According to a further aspect of the disclosure, methods of mitigating adverse effects of exposure to oxidizers, such as chlorinating and/or brominating agents, on biological and/or synthetic fibers are disclosed, comprising applying to said biological and/or synthetic fibers an effective amount of ascorbic acid.

According to a further aspect of the disclosure, methods of treating and/or preventing disorders of the mouth, including teeth, gums, buccal, and/or throat, such as, for example, gingivitis, periodontis, cavities, and oral wounds are disclosed, said methods comprising administering a composition comprising an effective amount of ascorbic acid to a mammal in need thereof. For example, disclosed herein are antioxidant mouth rinses comprising greater than 5% ascorbic acid by mass. In at least one embodiment, the antioxidant mouth rinse comprising greater than about 5% ascorbic acid by mass has a pH of greater than about 7, such as about 7.5.

In a further aspect of the disclosure, methods of sanitizing the surface of a material are disclosed, comprising exposing the surface of the material to an oxidant (e.g., a chlorinating agent), and thereafter treating said surface of the material with a composition comprising an effective amount of ascorbic acid.

In yet a further aspect of the disclosure, methods of treating biological chicken fibers during processing of a chicken carcass, by exposing the biological chicken fibers to a composition comprising an effective amount of ascorbic acid, such as, for example, by injecting said composition into the biological chicken fibers, are disclosed.

In various embodiments, salts and/or derivatives (including but not limited to oxidized forms) of ascorbic acid may be used in place of, or in addition to, ascorbic acid. Salts and/or derivatives of ascorbic acid would function similarly within the context of the disclosed compositions and methods. As non-limiting examples, esters or ethers of ascorbic acid may be used in the compositions and methods of the disclosure. Unless otherwise noted or individually recited, when the term "ascorbic acid" is used herein, it is intended to include salts (e.g. sodium ascorbate) and/or degradation products and/or derivatives (e.g. oxidized forms) thereof, including compounds of formula A, whether or not so stated. For example, when present within an aqueous solution, the term "ascorbic acid" as used herein is intended to include products formed as a result of ascorbic acid reacting with water and/or oxygen, such as, for example, dehydroascorbic acid.

Furthermore, as known, ascorbic acid has stereogenic centers in its structure, for example the carbons modified by the (R)- and (S)-indicators in the chemical name (R)-3,4-dihydroxy-5-((S)-1,2-dihydroxyethyl)furan-2(5H)-one. This disclosure contemplates use of any combination of stereoisomers of ascorbic acid, including isolated stereoisomers, and all mixtures thereof.

The phrases "effective amount of ascorbic acid" or "effective amount of a composition comprising ascorbic acid", and variations thereof, as used herein, are intended to include any amount of ascorbic acid (as defined herein to include salts, degradation products, and derivatives) that is sufficient to convert any or all of the N—Cl and/or N—Br groups bound to the biologic and/or synthetic fibers being treated into N—H. In at least one embodiment, an effective amount of ascorbic acid means an amount sufficient to mitigate (i.e. reduce to any degree or eliminate completely) the perceptible adverse effects of exposure to oxidizers, such as chlorinating or brominating agents. For example, in one embodiment, an effective amount of ascorbic acid would be an amount sufficient to reduce or eliminate an odor of chlorine from biologic and/or synthetic, such as, for example, to reduce or eliminate an undesirable "pool odor" present on the body and/or clothes of a swimmer.

In a further exemplary embodiment, an effective amount of ascorbic acid is an amount sufficient to reduce the number of N—Cl and/or N—Br bonds in biologic and/or synthetic fibers by at least about 50%. In further exemplary embodiments, an effective amount may reduce the number of N—Cl and/or N—Br bonds in biologic and/or synthetic fibers by at least about 60%, at least about 70%, at least about 80%, at least about 90%, at least about 95%, at least about 98%, or at least about 99%.

By way of example only, with reference to compositions according to the disclosure, an effective amount of ascorbic acid, salts, and/or derivatives (e.g., oxidative degradation products) thereof, may range from about 2% to about 38%, such as from about 2.5% to about 25%, within a solution. For example, a solution may comprise about 5% to about 25%, about 10% to about 20%, about 15% to about 18%, such as about 16.8% of compounds of formula A. In further exemplary embodiments, a solution may comprise about 16% to about 35% of ascorbic acid.

In further exemplary embodiments, a solution according to the disclosure may comprise a concentration of ascorbic acid ranging from about 0.5 to about 2 Molar. By way of non-limiting example, aqueous solutions may comprise about 0.3 to about 3 moles, such as about 0.5 to about 1.5 moles, or about 1.5 to about 3 moles, of compounds of formula A per one liter of water.

In at least one embodiment, an effective amount of ascorbic acid means a saturated aqueous solution of ascorbic acid. At standard temperature and pressure a "saturated solution of ascorbic acid" is commonly accepted to be a solution made of 330 grams of ascorbic acid per one liter of water. This concentration will vary as a function of temperature, as will be appreciated by those of skill in the art. In various embodiments, the disclosure relates to saturated solutions of ascorbic acid at any temperature, meaning the maximum amount of ascorbic acid that is soluble in water at the given temperature and pH.

In exemplary embodiments where treatment compositions are applied to reduce or eliminate adverse effects of exposure to chlorinating and/or brominating agents, e.g. the odor of chlorine and/or itching and/or skin irritation, the effective amount of ascorbic acid may vary. Choosing an effective amount is within the skill of those of skill in the art, and may, for example, be done empirically, using more ascorbic acid where the odor of chlorine and/or itching/and/or skin irritation persists after applying an initial amount of ascorbic acid. By way of example only, an effective amount of ascorbic acid may range from about 0.2 to about 10 grams, such as about 0.5 to about 5 grams, or such as about 1 to about 3 grams.

Under some circumstances, the ascorbic acid present in an aqueous solution may degrade via oxidative pathways upon exposure to air. Various embodiments of the disclosure relate, therefore, to aqueous solutions comprising any combination of ascorbic acid and mixtures of these oxidative degradation products, such as dehydroascorbic acid, including aqueous solutions comprising only said oxidative degradation products.

In various exemplary embodiments, the compositions and methods disclosed herein comprise ascorbic acid solutions having a pH of less than about 6, such as, for example, less than about 5, less than about 4, or less than about 3. In further embodiments, the ascorbic acid solutions may have a pH of between about 3 and about 4. In yet further exemplary embodiments, the ascorbic acid solutions may have a pH of about 2. In one embodiment, the pH of the ascorbic acid solutions may range from about 1.9 to about 2.2.

In further exemplary embodiments, the compositions and methods disclosed herein comprise ascorbic acid solutions having a pH in the range of about 5 to about 8, such as about 5 to about 7.5, about 6 to about 7, about 7 to about 7.5, or about 6. Compositions having a particular pH and concentration of ascorbic acid may be made by applying the Henderson-Hasselbalch equation for estimating the pH of a buffer solution.

In yet further exemplary embodiments, the ascorbic acid used in the compositions and/or methods described herein may be replaced with, or used in combination with, one or more acid, salt, and/or derivatives thereof, to form acidic solutions, such as, for example, acidic aqueous solutions. Any acid, salt, and/or derivative thereof that is safe for the intended application may be used. For example, one or more of the following acids may be used in an acidic aqueous solution contemplated by the disclosure: acetic acid, citric acid, aconitic acid, adipic acid, benzoic acid, caprylic acid, cholic acid, desoxycholic acid, erythorbic acid, ferulic acid, formic acid, glutamic acid, glycocholic acid, hydrochloric acid, lactic acid, linoleic acid, malic acid, nicotinic acid, oleic acid, pectinic acid, phosphoric acid, propionic acid, sorbic acid, stearic acid, succinic acid, sulfamic acid, sulfuric acid, tannic acid, tartaric acid, taurocholic acid, and/or thiodipropionic acid. As a further example, one or more of the following salts may be used in the compositions according to the disclosure: lauryl sulfate salts, laureth sulfate salts, sodium chloride, and sodium ascorbate. The compositions according to further embodiments may also comprise glycerin and/or menthol. As such, throughout the disclosure where compositions and methods comprising ascorbic acid, salts, and/or derivatives thereof are described, it should be understood that the ascorbic acid, salts, and/or derivatives may be replaced with, or used in combination with, one or more acid, salt, and/or derivative thereof.

However, according to additional exemplary embodiments of the disclosure where the composition is in the form of a solution, the compositions may be free or substantially free from components other than compounds of formula A and a solvent, such as water. For example, the compositions may be free or substantially free from $O_2$.

In one embodiment, the acidic solutions may have a pH of less than about 6, such as, for example, less than about 5, less than about 4, or less than about 3. In further embodiments, the acidic solutions may have a pH of between about 3 and about 4. In yet further exemplary embodiments, the acidic solutions may have a pH of about 2. In one embodiment, the pH of the acidic solutions may range from about 1.9 to about 2.2.

In further exemplary embodiments, the compositions and methods disclosed herein comprise solutions having a pH in the range of about 5 to about 8, such as about 5 to about 7.5, about 6 to about 7, about 7 to about 7.5, or about 6.

Exemplary compositions according to the disclosure may be aqueous or non-aqueous, and may be in any known form. For example, they may be solutions, powders, tablets, creams, gels, emulsions, etc. The compositions according to various embodiments of the disclosure may be packaged in any type of vessel or container that is useful for the specific formulation, and effective to dispense the composition. In at least certain exemplary embodiments, the vessel containing the composition according to the disclosure may be free or substantially free of $O_2$. For example, the composition may be applied or administered by dispensing or spraying it from an aerosol or non-aerosol container that is free or substantially free of $O_2$.

In one embodiment, for example, the compositions may be in the form of a tablet, such as an effervescent tablet, which may be placed in water or another solvent before use. In yet a further exemplary embodiment, the composition may be an aqueous solution.

As non-limiting examples of aqueous ascorbic acid compositions useful according to the disclosure, there may be any amount of (5R)-[(1S)-1,2-dihydroxyethyl]-3,4-dihydroxyfuran-2(5H)-one and dehydroascorbic acid present in various embodiments of the disclosure, as long as at least some amount of ascorbic acid, salts, and/or derivatives thereof is present, such as, for example, one of the following:

In one embodiment, the aqueous solution of ascorbic acid comprises greater than 99% (5R)-[(1S)-1,2-dihydroxyethyl]-3,4-dihydroxyfuran-2(5H)-one and less than 1% dehydroascorbic acid.

In one embodiment, the aqueous solution of ascorbic acid comprises from 95-100% (5R)-[(1S)-1,2-dihydroxyethyl]-3,4-dihydroxyfuran-2(5H)-one and from 0-5% dehydroascorbic acid.

In one embodiment, the aqueous solution of ascorbic acid comprises from 90-100% (5R)-[(1S)-1,2-dihydroxyethyl]-3,4-dihydroxyfuran-2(5H)-one and from 0-10% dehydroascorbic acid.

In one embodiment, the aqueous solution of ascorbic acid comprises from 80-95% (5R)-[(1S)-1,2-dihydroxyethyl]-3,4-dihydroxyfuran-2(5H)-one and from 5-20% dehydroascorbic acid.

In one embodiment, the aqueous solution of ascorbic acid comprises from 60-80% (5R)-[(1S)-1,2-dihydroxyethyl]-3,4-dihydroxyfuran-2(5H)-one and from 20-40% dehydroascorbic acid.

In one embodiment, the aqueous solution of ascorbic acid comprises from 30-60% (5R)-[(1S)-1,2-dihydroxyethyl]-3,4-dihydroxyfuran-2(5H)-one and from 40-70% dehydroascorbic acid.

In one embodiment, the aqueous solution of ascorbic acid comprises from 0.1-30% (5R)-[(1S)-1,2-dihydroxyethyl]-3,4-dihydroxyfuran-2(5H)-one and from 70-99.9% dehydroascorbic acid.

In another exemplary embodiment, the composition may be a soap composition. Soap compositions contemplated herein may comprise, inter alia, water, ascorbic acid, and soap. In one exemplary embodiment, the composition consists essentially of water, ascorbic acid, and soap.

Exemplary soap compositions according to the disclosure may be made, for example, by mixing (A) an aqueous solution of ascorbic acid as described herein with (B) a liquid soap composition. In various embodiments, the soap compositions according to the disclosure have a pH of less than about 6, such as, for example, less than about 5, less than about 4, or less than about 3. In further exemplary embodiments, the soap compositions according to the disclosure have a pH in the range of about 5 to about 8, such as about 5 to about 7.5, about 6 to about 7, about 7 to about 7.5, or about 6.

In another exemplary embodiment, the composition may be a foaming composition. Foaming compositions contemplated herein may comprise, inter alia, water, ascorbic acid, and a foaming agent.

Exemplary foaming compositions according to the disclosure may be made, for example, by mixing an aqueous solution of ascorbic acid with a foaming agent (e.g, an appropriate shampoo, soap, or body wash) to form a liquid that is capable of providing a foam when dispensed through a foaming hand soap dispenser. In various embodiments, the foaming compositions according to the disclosure have a pH of less than about 6, such as, for example, less than about 5, less than about 4, or less than about 3. In further exemplary embodiments, the foaming compositions according to the disclosure have a pH in the range of about 5 to about 8, such as about 5 to about 7.5, about 6 to about 7, about 7 to about 7.5, or about 6.

In addition to ascorbic acid, salts, degradation products, and/or derivatives thereof, the compositions of the disclosure may also optionally include other component(s) useful in compositions according to the intended application, as long as the additional component(s) do not substantially interfere with the intended function of the ascorbic acid. By way of non-limiting example, for applications intended to be applied to body and/or clothing fibers, such additional components may include, but are not limited to, emollients, preservatives, perfumes, thickeners, cleansing agents, etc. It may also be desirable in various embodiments that the additional components do not damage or otherwise adversely affect the fibers to which the composition is applied.

One of skill in the art would be able, through routine experimentation, to formulate acceptable compositions comprising an effective amount of ascorbic acid, salts, and/or derivatives thereof, and formulations thereof, for treatment of biological and/or synthetic fibers as described herein. As non-limiting examples, formulations comprising ascorbic acid:sodium ascorbate in a molar ratio of about 79:1, or comprising water:sodium ascorbate:ascorbic acid in a molar ratio of about 55.6:1.0:0.013 are contemplated.

Further aspects of the disclosure provide methods of mitigating adverse effects of exposure to oxidizers such as chlorinating and/or brominating agents, e.g. swimming pool chemicals and associated itching, irritation, and/or "pool odor." Said methods comprise treating biological and/or synthetic fibers with a composition according to the disclosure, e.g. applying an effective amount of a composition according to the disclosure to said fibers.

In at least one exemplary method, the effective amount of a composition according to the disclosure is applied by spraying the composition onto the body fibers of a subject, such as, for example, the skin and/or hair, or onto clothing. The composition according to the disclosure may be sprayed by any method known, such as, for example, an aerosol spray or a non-aerosol pump bottle.

In at least one exemplary embodiment, the composition according to the disclosure is applied by using a foaming composition comprising ascorbic acid, water, and a foaming agent. In some exemplary embodiments, the foaming composition is applied by dispensing said foaming composition through a dispenser (e.g. a foaming hand- or body-soap, or shampoo, dispenser), thereby creating a foaming lather, which is applied to the hair and/or skin.

In at least one exemplary embodiment of a subject exposed to chlorine and/or bromine in a swimming pool, the subject may optionally first rinse the residual pool water from his/her hair and/or body, then apply a composition according to the disclosure to his/her hair and/or body. In some embodiments, the person may thereafter immediately or substantially immediately wash the hair and/or body with soap, or may apply shampoo and/or conditioner. In further embodiments, the composition according to the disclosure is sprayed onto the hair and/or body after rinsing off residual pool water without subsequently immediately or substantially immediately washing the hair and/or body.

This disclosure also contemplates applying a composition according to the disclosure without first rinsing. When a composition according to the disclosure is applied without first rinsing, larger quantities may, in at least some embodiments, be required than when applied subsequent to rinsing.

In at least one exemplary embodiment, the method of applying a composition according to the disclosure is intended to include a method where a subject, such as a swimmer, applies an amount sufficient to reduce and/or eliminate his/her own "pool odor" and/or irritation as perceived by the subject. For a particular aqueous solution according to the disclosure, the effective amount required to reduce and/or eliminate the subject's odor and/or irritation may depend on the amount of hair and/or skin that the subject has. Generally speaking, a subject may adjust the amount of the composition applied based on his or her own observations—if the subject experiences "pool odor" and/or irritation following administration, more may be applied.

In various embodiments, the methods according to the disclosure relate to methods of treating hair comprising applying a composition as described herein. It is contemplated that a person with little or no hair would recognize that using a smaller amount of the composition provides effective reduction or elimination of "pool odor" and/or irritation, and thus, in at least certain embodiments, an effective amount may be less than in an embodiment where a person has a lot of hair.

The compositions according to the disclosure may, in various embodiments, be applied to the body and/or clothing fibers and immediately removed (e.g. by rinsing the fibers right away), or may be left on the fibers for a period of time after application. For example, the body and/or clothing fibers may be washed (e.g. with soap or shampoo) subsequent to the application of the composition.

As described herein, the disclosure is set forth with regard to "people" for ease of reference only. However, the invention is not limited to humans, but rather is intended to include any mammal having body fibers that can form an N—Cl or N—Br bond. As such, the use of the terms "swimmer" or "people" is intended to include any mammal that swims or is otherwise exposed to swimming pool chemicals such as chlorine and/or bromine.

The terms "pool chemicals" and the like are used generally throughout the disclosure for ease of reference, but should not be considered limited to chemical exposure in a swimming pool. Rather, any chemical such as chlorinating agents (e.g., hypochlorite salts such as calcium hypochlorite or sodium hypochlorite, hypochlorous acid) or brominating agents (e.g., bromine, salts comprising bromine, hypobromous acid, etc.) are intended to be included with reference to "pool chemicals" and the like, whether or not a person is actually exposed to those chemicals in a swimming pool.

The term "biological fibers" is intended to refer to fibers comprising proteins, such as those found in and from living beings, including but not limited to skin, hair, nails, muscle, and other fibrous tissues of mammals, as well as plant fibers. It is also intended that fibers from harvested animals that are no longer living, such as harvested poultry during processing, are included in the term "biological fibers," as these fibers likewise comprise proteins.

Further embodiments of the disclosure relate to methods of mitigating the adverse effects of exposing poultry, e.g. chicken, to chlorinated water during processing, said methods comprising treating poultry fibers with an effective amount of a composition according to the disclosure.

The poultry can be treated with compositions according to the disclosure according to any method. For example, in at least one exemplary method, the composition is applied by spraying an aqueous solution of ascorbic acid onto poultry after the poultry is removed from the chiller. In a further exemplary method, the composition is applied by submerging the poultry in an aqueous solution of ascorbic acid after the poultry is removed from the chiller. In yet a further exemplary method, the poultry is first removed from the chiller, then rinsed with plain water to remove excess chiller water, then treated with a composition according to the disclosure, as above. In at least certain exemplary embodiments, treating the poultry may optionally include a further step of rinsing the poultry to remove any residual ascorbic acid. In various embodiments, compositions according to the disclosure may be applied to the poultry fibers and immediately removed (e.g. by rinsing the fibers right away), or may be left on the poultry fibers for a period of time after application. It should be noted, however, that any method of treating poultry with compositions as described herein is intended to be within the scope of the disclosure.

In a further exemplary embodiment, the poultry is treated with a composition according to the disclosure by injecting the said composition into the meat and/or skin of the poultry, for example by injecting a brine solution comprising ascorbic acid. Without being bound by any theory, it has been observed that injecting solutions comprising an antioxidant (e.g., ascorbic acid) provides reducing equivalents, which quench residual oxidants (such as lingering chlorine) after exposure to chlorinated water. For example, by injecting chicken with an aqueous solution comprising ascorbic acid after rinsing the chicken with chlorinated water, one can lower the amount of residual chlorine present in the chicken.

In one sense, an effective amount of a composition for treating poultry fibers according to the disclosure refers to an amount sufficient to reduce the adverse effects of chlorine, i.e. lessening the adverse effects perceived by the consumer, such as color bleaching, and malodor. In another context, an effective amount of a composition for treating poultry fibers according to the disclosure refers to an amount sufficient to reduce the amount of residual chloride and/or hypochlorite after expose to aqueous chlorine (e.g., chlorine, hypochlorite, etc. in water) measured in a laboratory vis-à-vis a control group that is not exposed to ascorbic acid.

For various exemplary aqueous solutions of this invention, the poultry producer's requirements may depend on the volume and size of the poultry undergoing processing and/or the degree to which that poultry is chlorinated. Generally speaking, greater amounts of poultry and higher degrees of chlorination will require higher quantities of ascorbic acid to mitigate the unwanted chlorination of the poultry. A poultry processor may adjust the amount of ascorbic acid applied based on his/her observations (e.g., if the observer notices chlorine odor, bleaching, and/or measures elevated levels of residual chlorine) following treating the poultry with aqueous ascorbic acid, then that indicates that more ascorbic acid should be used.

Further embodiments of the disclosure are related to methods for treating biological and/or synthetic fibers, such as may be found in some textiles, e.g. towels, swimming attire, swimming accessories, etc., exposed to oxidizing agents, such as those exposed to chlorinated and/or brominated pool water, with an aqueous solution of ascorbic acid. Such treatment may reduce the "pool odor" of, and/or "wear" associated with such exposure on, the textiles. For example, treating swimming attire exposed to chlorinated and/or brominated pool water with a composition according to the disclosure has been found to reduce the "pool odor" of that swimming attire. Treating swimming attire exposed to chlorinated and/or brominated pool water with composition according to the disclosure has also been found to reduce the oxidative damage done to the swimming attire, thereby prolonging its life and reducing the fading and/or discoloration of its materials, typically associated with such textiles. As used herein, the terms "clothing" and "textiles" should be considered interchangeable in that when the term "clothing" is used, it is intended to include any textiles within the scope of the disclosure. For example, when reference is made to treatment of a swimmer's clothing or attire, it is intended that a swimmer's towel, etc., is included in said disclosure and claims. It should also be noted that textiles are intended to be included as biological and/or synthetic fibers, as textiles are traditionally made up of fibers such as plant and/or animal fibers, or may be manmade, such as polymer fibers.

In at least one exemplary method, an effective amount of a composition according to the disclosure is applied by treating the textiles with an aqueous solution of ascorbic acid, such as by applying the composition by contacting the textiles with said composition. Any method for treating textiles known in the art may be used, such as, for example, spraying the textile with the composition using an aerosol or non-aerosol spray; immersing the textile into the composition; and/or washing the textile with a soap composition comprising ascorbic acid, as described herein.

In one exemplary embodiment, the textiles may optionally first be rinsed with standard tap water before applying the composition according to the disclosure, and optionally thereafter be rinsed a second time with standard tap water after the application. In another embodiment, the composition according to the disclosure is applied without first rinsing the textiles with standard tap water. The textiles may optionally be washed as normal, subsequent to the application of the composition according to the disclosure.

In at least one exemplary embodiment, the textiles may be treated with about 0.2 to about 10 grams of ascorbic acid, such as about 0.5 to about 5 grams of ascorbic acid, or about 1 to about 3 grams of ascorbic acid.

In further embodiments according to the disclosure, methods for reducing biological fibers are also contemplated. Such methods include steps of (1) identifying biological fibers which are capable of undergoing reduction, and (2) applying a composition according to the disclosure to said biological fibers. In further embodiments, said methods include a step of applying a composition according to the disclosure to said biological fibers. In various embodiments, for example, the biological fibers which are capable of undergoing reduction include those of the mouth, including teeth, gums, buccal, and/or throat.

In further embodiments according to the disclosure, methods for sanitizing biological and/or synthetic fibers are also contemplated. Such methods include steps of (1) first treating said material with an oxidizing agent, and (2) thereafter treating the surface and/or material with a composition according to the disclosure. In further embodiments, said methods include a step of applying a composition according to the disclosure to said surface and/or material. In at least one embodiment, the methods include one or more aqueous rinsing steps. As used herein "sanitizing" means cleaning. As used herein "disinfecting," means killing living organisms (e.g., bacteria). As used herein, "synthetic fibers" is intended to include fibers that do not contain protein, and are typically man-made.

In further embodiments according to the disclosure, methods of administering vitamin C to a mammal are contemplated, said method comprising administering a composition according to the disclosure via a vessel that is free or substantially free of $O_2$. Ascorbic acid is known to degrade when allowed to stand in the presence of oxygen. Oxygen is a natural component of the Earth's atmosphere, where it resides in air and water. It has been found that storing the compositions according to the disclosure in an oxygen-free environment provides for many advantages, such as prolonging storage and shelf life.

Aqueous ascorbic acid solutions according to various embodiments of the disclosure may thus optionally be made oxygen-free, for example by bubbling an inert gas through the solution, thereby driving out any oxygen dissolved in the water. Alternatively, aqueous ascorbic acid solutions may be made by mixing ascorbic acid with water, sealing the solution off from the environment (e.g., by sealing the solution in a bottle), and allowing the bottle to stand until the oxygen sealed inside the bottle is consumed by the ascorbic acid in the solution. By way of example only, methods of administering ascorbic acid to mammals may comprise dispensing a composition according to the disclosure by spraying said composition, e.g. using an aerosol spray or a non-aerosol pump.

In yet further embodiments, methods of preventing oxidative damage incident to radiation therapy are contemplated, said methods comprising administering a composition according to the disclosure to a patient who will undergo radiation therapy. Some cancer patients are treated via a course of radiation therapy. Throughout the course of that therapy, many of those patients present with oxidative damage to the inside of the mouth, such as sores. These sores are believed to arise from oxidative damage incident to the radiation therapy. Disclosed herein are methods of alleviating or preventing the oxidative damage incident to radiation therapy comprising contacting the patient's oral cavity with a composition according to embodiments of the disclosure.

In further embodiments, methods of lowering the concentration of reactive oxygen species are contemplated, said methods comprising administering a composition according to the disclosure. Reactive oxygen species (also referred to as "free radicals") are known to damage healthy mammalian cells by reacting with the cells, thereby oxidizing the cells. Such reactive oxygen species can be generated by radiation, ultraviolet light, heat, chemical agents, etc. Where this oxidative damage presents at the surface of a mammal (e.g., the mammal's exterior, such as the skin), the reactive oxygen species can be quenched by applying a composition according to this disclosure.

Although the present disclosure herein has been described with reference to various exemplary embodiments, it is to be understood that these embodiments are merely illustrative of the principles and applications of the present disclosure. Those having skill in the art would recognize that various modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

It will be appreciated that there is an implied "about" prior to all numerical values recited herein, whether or not so stated. It should also be understood that the precise numerical values used in the specification and claims form additional embodiments. Efforts have been made to ensure the accuracy of the numerical values disclosed herein. Any measured numerical value, however, can inherently contain certain errors resulting from the standard deviation found in its associated measuring technique. As used herein, reference to percent is intended to indicate wt %, relative to the weight of the composition.

Furthermore, other embodiments of the disclosure will be apparent to those skilled in the art from consideration of the specification and practice of the invention disclosed herein. It is intended that the specification and examples be considered as exemplary only, with a scope and spirit being indicated by the claims.

Finally, it is noted that, as used in this specification and the appended claims, the singular forms "a," "an," and "the," include plural referents unless expressly and unequivocally limited to one referent, and vice versa. Thus, by way of example only, reference to "a composition" can refer to one or more compositions, and reference to "a salt of ascorbic acid" can refer to one or more salts of ascorbic acid. As used herein, the terms "comprise", "comprises", "comprising", "contain", "contains", "containing", "have", "having", "include", "includes", and "including" are intended to be non-limiting, such that recitation of an item or items is not to the exclusion of other like items that can be substituted or added to the recited item(s).

EXAMPLES

The following examples are illustrative only, and are not intended to be limiting of the invention, as claimed.

Example 1

At standard temperature and pressure, 330 grams of ascorbic acid were dissolved in 1 L of water. This solution 1 was then applied to hair that had been exposed to swimming pool chemicals.

Example 2

At standard temperature and pressure, 300 grams of ascorbic acid were dissolved in 1 L of water. This solution 2 was then applied to hair that had been exposed to swimming pool chemicals.

Example 3

At standard temperature and pressure, 270 grams of ascorbic acid were dissolved in 1 L of water. This solution 3 was then applied to hair that had been exposed to swimming pool chemicals.

Example 4

At standard temperature and pressure, 240 grams of ascorbic acid were dissolved in 1 L of water. This solution 4 was then applied to hair that had been exposed to swimming pool chemicals.

Example 5

At standard temperature and pressure, 210 grams of ascorbic acid were dissolved in 1 L of water. This solution 5 was then applied to hair that had been exposed to swimming pool chemicals.

Example 6

At standard temperature and pressure, 180 grams of ascorbic acid were dissolved in 1 L of water. This solution 6 was then applied to hair that had been exposed to swimming pool chemicals.

Example 7

At standard temperature and pressure, 150 grams of ascorbic acid were dissolved in 1 L of water. This solution 7 was then applied to hair that had been exposed to swimming pool chemicals.

Example 8

At standard temperature and pressure, 120 grams of ascorbic acid were dissolved in 1 L of water. This solution 8 was then applied to hair that had been exposed to swimming pool chemicals.

Example 9

At standard temperature and pressure, 90 grams of ascorbic acid were dissolved in 1 L of water. This solution 9 was then applied to hair that had been exposed to swimming pool chemicals.

Example 10

At standard temperature and pressure, 60 grams of ascorbic acid were dissolved in 1 L of water. This solution 10 was then applied to hair that had been exposed to swimming pool chemicals.

Example 11

At standard temperature and pressure, 30 grams of ascorbic acid were dissolved in 1 L of water. This solution 11 was then applied to hair that had been exposed to swimming pool chemicals.

Example 12

At standard temperature and pressure, 180 grams of ascorbic acid were dissolved in 1 L of water. The resulting solution 12 was transferred into 3 oz spray bottles. Following swimming in a chlorinated swimming pool, a subject's skin and hair were rinsed with warm shower water for about 30 seconds. Then, the solution 12 was applied to the subject by spraying the solution onto the skin and hair. A total of 10 mL of solution 12 was evenly sprayed onto the subject's skin, and a total of 20 mL of solution 12 was evenly sprayed onto the subject's hair. The subject was then allowed to wash and rinse their skin with soap, and shampoo, rinse, and condition their hair, as normal. The shampoo was applied to the hair without first rinsing out the solution 12, so that the shampoo and lather distributed the solution.

Example 13

At standard temperature and pressure, 240 grams of ascorbic acid were dissolved in 1 L of water. The resulting solution 13 was transferred into 3 oz spray bottles.

Six swimmers were immersed in a swimming pool (Washington Lee High School swimming pool in Arlington, Va.) for a period of one hour. Each of the subjects was assigned to one of two groups: three to the Swim Spray group and three to the control group.

After exiting the pool, the three swimmers in the Swim Spray group rinsed their skin and hair with warm shower water for about 30 seconds and then applied the solution 13 by spraying the solution onto their skin and hair. A total of 5 mL of solution 13 was sprayed onto each subject's skin, and a total of 10 mL of solution 13 was sprayed onto each subject's hair. After exiting the pool, the three swimmers in the control group similarly rinsed their hair and skin with warm shower water, but did not apply the solution.

All six swimmers were then allowed to wash and rinse their skin with soap, and shampoo, rinse, and condition their hair, as normal. All subjects used the same shampoo and conditioner (Garnier Fructis for regular hair). In the Swim Spray group, the shampoo was applied to the hair without first rinsing out the solution 13, so that the shampoo and lather distributed the solution. Both groups then towel dried and waited for 30 minutes.

After 30 minutes, water was applied to a 3 cm×3 cm area of the subject's forearm, by gently swabbing with a warm, damp cloth. The subjects were then smelled by a blind judge (i.e., having no knowledge of whether any subject did or did not use the solution). The judge noted that each member of the control group smelled like "pool" or "chlorine," whereas the judge found that odor either "faint" or "not at all" for the members of the Swim Spray group.

The experiment was repeated, and consistent results were obtained.

Example 14

To a beaker containing 200 mL deionized water, was dissolved 40 g sodium ascorbate, making a 1 M solution. 440 mg of ascorbic acid was slowly added to the solution and stirred vigorously until all powders were in solution. The pH of the resulting solution was measured and determined to be 6.

The resulting solution was transferred into 4 oz plastic (PET) bottles equipped with pump sprayers. The solution was tested for efficacy by applying it to swimmers via spraying after exposure to chlorinated water as described above. The solution was determined to be effective for mitigating chlorine odor as perceived by swimmers in the field.

What is claimed is:

1. An aqueous composition comprising water, ascorbic acid, and sodium ascorbate, wherein:
    said ascorbic acid and sodium ascorbate are present in a combined amount of about 5 to 25 wt %,
    said water is present in about 75 to 95 wt %,
    said composition has a pH of about 6 to about 7.5, and
    the sodium ascorbate and ascorbic acid are present in a sodium ascorbate: ascorbic acid molar ratio of about 80:1 to about 2000:1.

2. The composition of claim 1, wherein the ascorbic acid and sodium ascorbate are present in a combined amount of about 10 to 20 wt %.

3. The composition of claim 2, consisting essentially of water, ascorbic acid, and sodium ascorbate.

4. The composition of claim 2, having a pH of about 6 to about 7.

5. The composition of claim 2, having a pH of about 6.

6. A method of dechlorinating biological fibers, said method comprising contacting said biological fibers with an aqueous composition of claim 1, wherein the biological fibers are selected from the group consisting of hair, skin, and nails.

* * * * *